United States Patent [19]

Bayerl et al.

[11] Patent Number: 6,051,372
[45] Date of Patent: Apr. 18, 2000

[54] TEMPLATE INDUCED PATTERNING OF SURFACES AND THEIR REVERSIBLE STABILIZATION USING PHASE TRANSITIONS OF THE PATTERNED MATERIAL

[75] Inventors: Thomas Bayerl, Würzburg; Gero Decher, Kehl-Marlen; Thomas Braunschweig, Leipzig, all of Germany

[73] Assignee: Nimbus Biotechnologie GmbH, Leipzing, Germany

[21] Appl. No.: 08/925,622

[22] Filed: Sep. 9, 1997

[51] Int. Cl.[7] .......................... C12Q 1/00; G01N 33/543; B01J 37/36
[52] U.S. Cl. .................... 435/4; 435/6; 435/7.1; 435/287.1; 436/518; 530/412; 530/413; 502/7; 502/439
[58] Field of Search .............................. 435/7.2, 6.4, 871, 435/287.1, 287.9, 7.1; 530/412, 413; 427/222; 436/518, 501, 63, 71; 502/402, 439, 7

[56] References Cited

U.S. PATENT DOCUMENTS 5,310,648  5/1994  Arnold et al. .............................. 435/5

Primary Examiner—Keith D. MacMillan
Assistant Examiner—P. Ponnaluri
Attorney, Agent, or Firm—Antonelli, Terry, Stout & Kraus, LLP

[57] ABSTRACT

A two-dimensional patterning of a three-dimensional surface by a template molecule (or object) involving non-covalent interactions between the template and the surface and the reversible fixation of the pattern by undergoing a phase transition in the patterned material. In this invention the surface provides a multitude of mobile functional groups (matrix) which are spatially arranged by the interaction with the template, the template selects and arranges only those groups out of a multitude of functional groups which allow for a maximum of interaction between the template and the surface. The resulting pattern is then stabilized by reducing the mobility of all functional groups present on the surface by undergoing a phase transition to a state of high surface viscosity. After separation of the template and the patterned surface, the pattern on the surface is used for recognition, separation or catalytic purposes.

20 Claims, 4 Drawing Sheets

TEMPLATE INDUCED PATTERNING OF SURFACES AND THEIR REVERSIBLE STABILIZATION USING PHASE TRANSITIONS OF THE PATTERNED MATERIAL

FIELD OF THE INVENTION

The present invention relates to a method of preparing lipid monolayers and bilayers capable of forming molecular imprints, and a method of using such lipid layers for molecular separation, isolation, purification or catalyzation.

BACKGROUND OF THE INVENTION

Complex surfaces with three-dimensional topologies possessing a specific spatial arrangement of chemical functional groups are the basis for phenomena such as recognition, separation or catalysis. The fabrication of such systems using organic or biological molecules as templates has been termed "molecular imprinting". Most of these systems are created by interaction of a template molecule with either a pre-formed polymer or by polymerization of monomers in the presence of a template[1, 2]. (See the list of corresponding publications (1)–(14) at the end of the specification). The resulting structures are bulk polymers in which the template leaves behind cavities, which are more or less complementary to the shape and spatial distribution of functional groups of the template. Based on the pioneering work of the formation of monomolecular layers of alkylsilanes on glass or quartz surfaces by chemisorption from solution by J. Sagiv et al.[3], it was shown that planar solid surfaces can also be patterned and that such systems show selective molecular recognition[3-5]. The use of the molecular self-organization property of amphiphilic molecules offers further advantages. The two-dimensional diffusion of lipid and lipid-analog molecules in Langmuir monolayers at the air/water interface allows the formation of two-dimensional patterns in such monolayers by binding template molecules from the subphase[6-8]. Such structures have been studied not only at the water surface, but also after transfer onto solid supports[9, 10]. The latter systems are today the only systems which do not employ either polymerization or cross-linking in order to stabilize the imprinted structure, but it has not been shown that the template molecules can be removed from the patterns without loss of the imprint. Finally, imprinted patterns have also been created on the surfaces of lipid bilayer membranes of liposomal assemblies using polymerizable lipids with specific functional groups (e. g. histidine tags)[11-13]. In this case the patterns were stabilized by polymerization of the lipid matrix[11].

None of the systems described above use or claim the use of lipids or lipid-like amphiphiles with polar or ionic headgroups for pattern formation via for example electrostatic or other reversible non-covalent interactions with templates. Furthermore the reversible formation of two-dimensional patterns has never before been described and molecular imprints have never been stabilized in a non-covalent way, e.g. by a physical phase transition, which allows to create and erase such imprints as desired.

SUMMARY OF THE INVENTION

It is an object of the present invention to provide a composition which changes its dynamic state (molecular order or orientation or both) through non-covalent interaction with a template object comprising: imprinted amphiphilic molecules having hydrophobic tail groups and hydrophilic head groups which form a surface at a solid/liquid interface; wherein the amphiphilic molecules within the surface spatially complement a portion of a template object brought in close contact with the surface to form a three-dimensional molecular imprinted surface; and wherein the composition can be reversibly switched between a semi-fluid or fluid state and a semi-solid or solid state by variation of a physical parameter of the composition.

Another object of the invention is to provide a method of separating a predetermined biological molecule or particle from a material that contains the predetermined biological molecule or particle using a molecular imprinted surface, comprising the steps of:

(a) contacting a molecular imprinted surface exhibiting three-dimensional molecular imprints of a portion of a predetermined biological molecule or particle, wherein the imprinted surface provides specific recognition and binding of the predetermined biological molecule or particle to the surface;

(b) separating the imprinted surface from the predetermined biological molecule or particle; and (c) recovering the predetermined biological molecule or particle from the molecular imprinted surface.

Still another object of the invention is to provide a catalytic surface comprising imprinted amphiphilic molecules having hydrophobic tail groups and hydrophilic head groups which form a surface at a solid/liquid interface; wherein the amphiphilic molecules within the surface spatially complement a portion of a template object brought in close contact with the surface to form a three-dimensional molecular imprinted surface; wherein the template object is complementary to a complement of a catalytic center, and wherein the composition can be reversibly switched between a semi-fluid or fluid state and a semi-solid or solid state by variation of a physical parameter of said composition.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DETAILED DESCRIPTION OF THE INVENTION

As used herein, the term "template" refers to a three-dimensional object which can be imprinted on a suitable medium by bringing it in contact with this medium and removing it from the medium again. Here the medium is sufficiently soft to ensure that the three-dimensional structure is not changed upon contact with the medium but sufficiently rigid to ensure that the imprint is retained in the medium after the removal of the three-dimensional object. A template can be, for example, an organic molecule, an inorganic crystal, a colloid, a protein, a peptide, a DNA or an antibody, termed herein as "macromole-cules", but also a cell organellae or a whole cell, a bacterium or a virus. The template must be larger than at least two chemical functional groups in the medium to be imprinted and smaller than the device which holds the medium to be imprinted.

As used herein, the term "surface" refers to a thin organic film as the medium, exhibiting surface properties that allow its local structuring in three dimensions by means of a template. It is understood that the constituent molecules of the thin organic film can diffuse laterally under certain conditions and exhibit a state of molecular order that is significantly higher than what the same molecules would exhibit as monomers in solution. A surface can be, for example, a lipid bilayer. As used herein, the term "predetermined biological molecule or particle" refers to a substance or structure which has been selected as a template for imprinting at a surface.

As used herein, the term "molecular imprint" refers to an imprint of a template at a surface with a resolution comparable to the spacing of chemical functional groups of the surface that complements part of the contour of the template and which remains stable after the separation of template and surface. For example, the use of a particular macromolecule as a template for imprinting should give a pattern of local indentations and protrusions within the surface with its internal three-dimensional structuring being sufficiently resolved to make it highly distinguishable from that of other macromolecules.

The main objective of the present invention is the provision of a surface that is three-dimensionally structured at a sub-molecular level in such a way that it complements spatially part of the outer contour of a predetermined biological molecule or particle. This molecularly imprinted surface will allow the predetermined biological molecule or particle to bind to the surface with a higher affinity as compared to a non-imprinted surface, even under conditions where specific recognition and binding takes place under competitive conditions, i.e. in situations where other macromolecules or biological particles can access the surface as well. Thus, specific recognition and binding between the imprinted surface and the predetermined biological molecule or particle is obtained by the three-dimensional surface profile of the imprinted surface and not by the use of any specific binding moieties attached to the surface constituent molecules. It should be clear that a single template object may generate several imprints in the composition of matter to be imprinted depending on the orientation of the template object with respect to the surface to be imprinted. Furthermore, the surface that is provided by the invention can be molecularly imprinted with the predetermined biological molecule or particle used as a template in a reversible fashion, that is, the imprint can not only be retained at the surface over a prolonged period of time but can also be erased at any time to give a non-specifically structured surface again that can at a later stage be imprinted with another predetermined biological molecule or particle as a second template which has no structural or whatsoever relationship with the one used as the first template. The process of storage and deletion of information imprinted at the surface can be repeated many times just by changing the template object and a single physical parameter of the system.

The three-dimensional molecular imprinted surfaces have applications in diagnostics, separation, especially bioseparation and manufacturing. If the template object is complementary to the complement of a catalytic center, e.g. the active site of an enzyme, one may also envision the use of the imprint as a catalytic surface. If the surface is used as a diagnostic, a chemiluminescent compound or radiolabel may be incorporated into the template molecule, surface, or both, as necessary.

As used herein, the term "bilayer" refers to a curved or planar bi-molecular layer, with each monolayer referred herein as "leaflet" and with the molecules that constitute the bilayer being either in a disordered and highly dynamic state referred herein as "fluid phase state" or in a more ordered and less dynamic state referred herein as the "gel- or crystalline phase state". The bilayer consists of at least two species of bilayer forming molecules, herein referred as "amphiphiles" (for example, two types of phospholipids), that differ for example by their overall length. Additional differences are possible. The bilayer can be switched between the two states by adjusting one physical parameter, the temperature, being either below or above a certain value referred herein as the "phase transition temperature". The fluid phase state exists above the phase transition temperature and is mainly characterized by its extreme softness and a high, long range lateral mobility of the amphiphiles along the bilayer plane, the latter herein referred as "lateral diffusion". In contrast, the main features of the gel- or crystalline phase state which exists below the phase transition temperature are its rigidity and the lack of lateral diffusion while intra-molecular high frequency motions (vibrations and rotations) of the amphiphiles are retained.

As used herein, the term "non-specific attractive interaction" refers to any interaction between the bilayer and the template that leads to a contact between them which is sufficiently close to produce a molecular imprint. The interaction needs not to rely on the presence of any specific interaction moieties attached to the bilayer. An example for a non-specific attractive interaction is the use a bilayer containing a percentage of amphiphiles carrying an excess electrical charge of opposite sign to that of the template. Another example is an electrically neutral bilayer on a solid support with the support exhibiting unscreened surface charges of opposite sign to that of the template.

The invention provides a surface exhibiting selective binding interactions with a template object, for example a biological molecule or particle through a local three-dimensional structuring of the surface that complements with a part of the outer surface structure of the biological molecule or particle, thus representing a realization of a "molecular key-lock" principle. Furthermore, the invention also provides a method of imprinting the surface with a predetermined biological molecule or particle used as a template.

One embodiment of the method may consist of the following steps. (a) Combining the template with a bilayer under conditions where the bilayer is in a fluid phase state and where a non-specific attractive interaction exists between the bilayer and the template, leading to an adsorption of the latter at the bilayer surface. (b) Allowing the optimization of the contact between the bilayer forming molecules (the amphiphiles) and the three-dimensional contour of that part of the predetermined biological molecule or particle that faces the bilayer by means of lateral diffusion of the amphiphiles and the surface diffusion of the adsorbed predetermined biological molecule or particle. (c) Formation of a molecularly imprinted bilayer surface by inducing a transition of the bilayer from its fluid phase state to a gel- or crystalline phase state. This is equivalent to an immobilization of the amphiphiles of different length at the optimum contact positions with respect to the contour of the adsorbed predetermined biological molecule or particle. A bilayer in the gel- or crystalline phase state exhibits sufficient rigidity and immobility of its components to retain this "frozen-in" distribution of the amphiphiles over a prolonged period of time. (d) Removal of the template object from the imprinted bilayer surface.

Virtually all biological molecules or particles that possess a net electrical charge in a solution at neutral pH value exhibit a spatial distribution of their electrically charged moieties. Thus, attractive Coulomb interaction can be achieved between those parts of the molecule or particle where either positive or negative charges are concentrated in surplus and a surface exhibiting the corresponding opposite charge. For the special case of proteins, the surface charge distribution is determined by the unique arrangement of surface amino acids. For example, myelin basic protein (MBP) can bind this way from a solution at neutral pH value both to anion- or cation exchanging gels of a standard ion exchange chromatography column, but at different binding constants. Such interactions can be considered as weak compared to those where specific binding moieties between the molecule or particle and the surface are involved but sufficiently strong to keep the molecules in contact with the surface. Furthermore, the Coulomb interaction of a biological molecule or particle with a charged surface is a rather unspecific process since structurally different molecules or particles may interact with the same surface at a similar binding constant. Other rather nonspecific and comparatively weak interactions between a surface and a biological molecule or particle are possible by means of van der Waals or hydrophobic forces. However, since the prerequisites for the formation of a molecular imprinted surface is the adsorption of the predetermined biological molecule or particle at the bilayer surface to be imprinted, each one of the above mentioned non-specific interaction mechanisms may be sufficient.

Figure 1A:
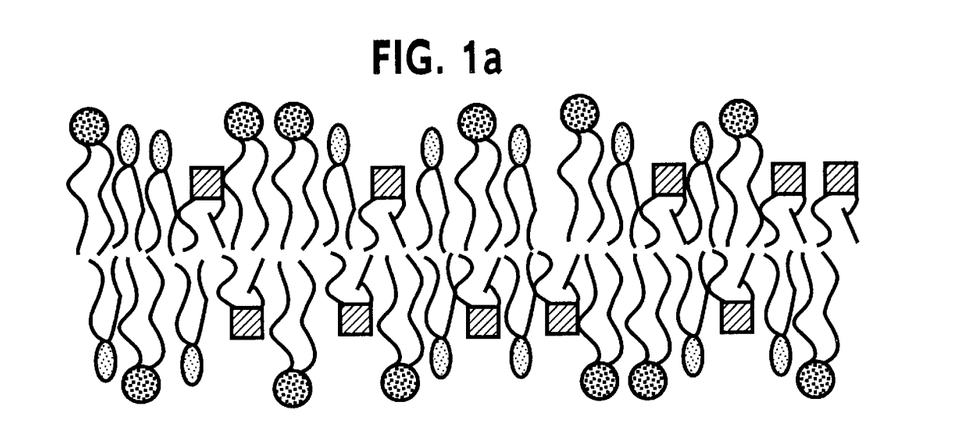
FIG. 1a shows a side-view schematic depiction of a bilayer consisting of amphiphiles species of different molecular length and/or headgroup structure. The given example is a drastic oversimplification and shows an exemplary case in which the bilayer is composed of three different amphiphiles.
Figure 1B:
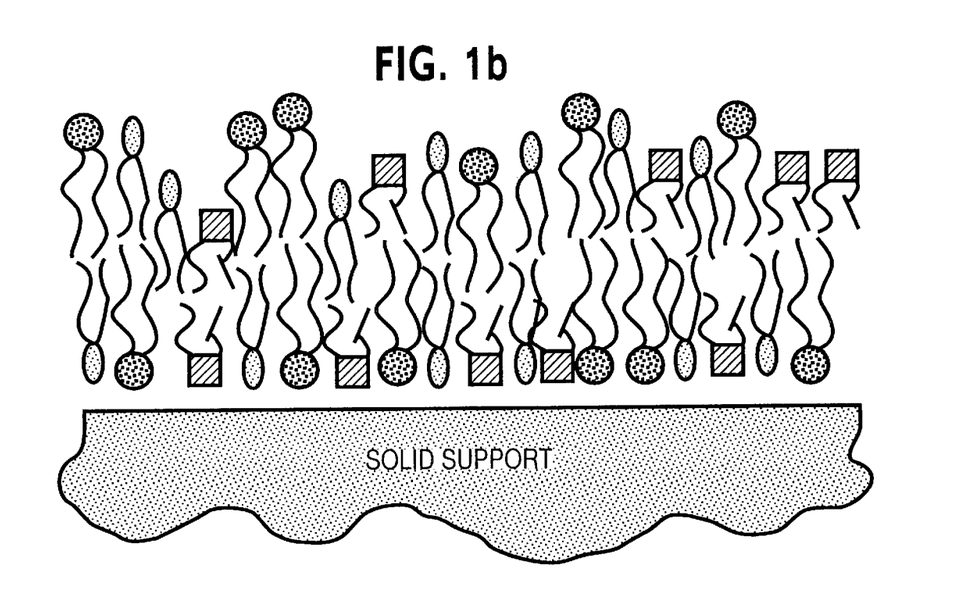
FIG. 1b shows a side-view schematic depiction of the effect of the presence of a solid support on the arrangement of the amphiphiles of different molecular length and/or headgroup structure within the bilayer.

Bilayers can be prepared by swelling amphiphiles like lipids or lipid analogs in excess water at temperatures above the phase transition temperature. In particular, bilayers exhibiting an excess electrical charge at neutral pH value can be prepared using anionic or cationic bilayer forming amphiphiles, preferentially in a mixture with electrically neutral (zwitterionic) bilayer forming amphiphiles to give a lipid bilayer that can interact via Coulomb interaction with biological molecules or particles. Furthermore, in addition to the charged or neutral hydrophilic parts of the amphiphiles, the bilayer can be prepared by using amphiphiles of different overall molecular length. For example, lipids can be used which differ in their hydrophobic tail length. The result can be a bilayer with local differences in its thickness owing to an arrangement of the constituent amphiphiles that minimizes the total interaction free energy of the system for a given geometrical constraint imposed by the different molecular lengths. As a consequence, the surface of the bilayer may become three-dimensionally structured at a molecular level, with some long amphiphiles protruding the surface and other short amphiphiles forming moulds in between. A sketch of such a (at sub-molecular level) wavy bilayer surface structure is given for the case of phospholipids as amphiphiles in FIG. 1a. The amplitude of the structuring in the direction normal to the bilayer plane may be further enhanced by the presence of a solid support. As used herein, the term "solid supported bilayer" refers to a bilayer attached to a smooth solid surface in such a way that one bilayer leaflet faces the solid surface but is separated from it by an ultrathin water layer. The attractive van der Waals interaction that keeps the bilayer attached to the solid surface causes each constituent amphiphile to approach the solid surface through the water layer as close as 10–20 Å. Below this separation distance, strong repulsive interactions dominate. As a result, the structuring of the bilayer that reflects the different lengths of the amphiphiles is enhanced for the bilayer leaflet facing the bulk. This situation is depicted for the case of phospholipids as amphiphiles in FIG. 1b. Note that FIG. 1b represents an exaggeration in the sense that in reality forces acting at the lipid headgroup/tail interfaces of the bilayer will partly compensate the attractive force between each lipid and the solid surface. The time scale over which such a local structuring is stationary will depend on the overall dynamical state of the bilayer. For lipid bilayers in the fluid phase state, where lateral diffusion of the lipids with typical diffusion constants in the order of $10^{-12}$ m$^2$/s can average out the local deviations of the bilayer thickness by diffusional jumps between adjacent lipids at a frequency in the order of $10^8$ Hz, this process can be considered as a mere thickness fluctuation. However, in the gel- or crystalline phase state where the lateral diffusion is virtually frozen, this local structuring can be considered as stationary and thus stable over a prolonged period of time.

The adsorption of a predetermined biological molecule or particle as a template to the bilayer leaflet facing the bulk of a solid supported bilayer under fluid phase conditions by at least one of the above mentioned nonspecific attractive interactions (Coulomb-, van der Waals- or hydrophobic forces) will cause a rearrangement of the laterally mobile amphiphiles in the bilayer area that is covered by the template according to the following objectives. (a) Neutral (zwitterionic) amphiphiles in the bilayer will arrange by thermal motions like lateral diffusion in order to minimize their free energy under the constraint that this particular part of the bilayer is sandwiched between a smooth solid surface (the solid support) and a three-dimensional structured surface imposed by the template. As a result, long amphiphiles will enrich in regions where the template exhibits moulds or fold ins while short amphiphiles will concentrate around regions where protrusions of the template press into the bilayer (b) Charged lipids in the bilayer leaflet facing the template will assemble at positions where they can complement opposite surface charges exposed by the template towards the bilayer. Thermal processes like lateral diffusion may oppose both processes (a) and (b) to a certain degree, leading to a non-equilibrium state of the particular bilayer area that consists of structured and non-structured regions at any instant. This is termed as a dynamic structuring in the following.

Figure 2A:
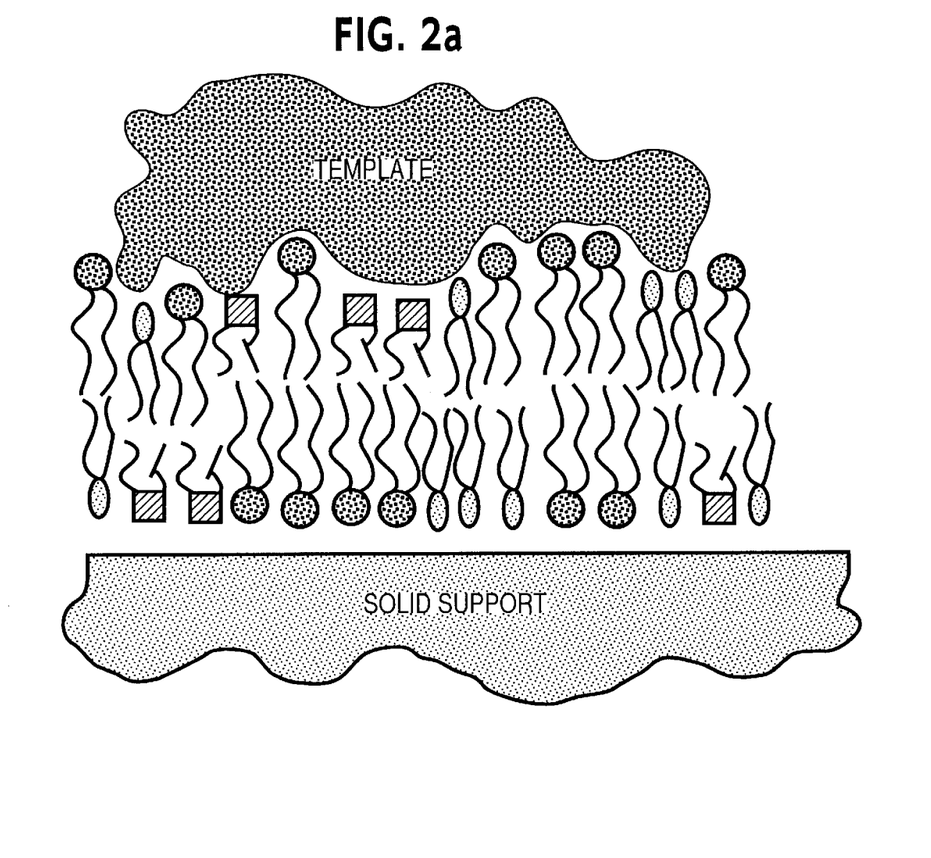
FIG. 2a shows a side-view schematic of the dynamic three-dimensional structure of a supported bilayer consisting of three amphiphiles of different molecular length and/or headgroup structure during reversible non-covalent interaction with a single template object in the fluid phase state of the bilayer. Note that the type of interaction between template object and bilayer is not specified in this example.
Figure 2B:
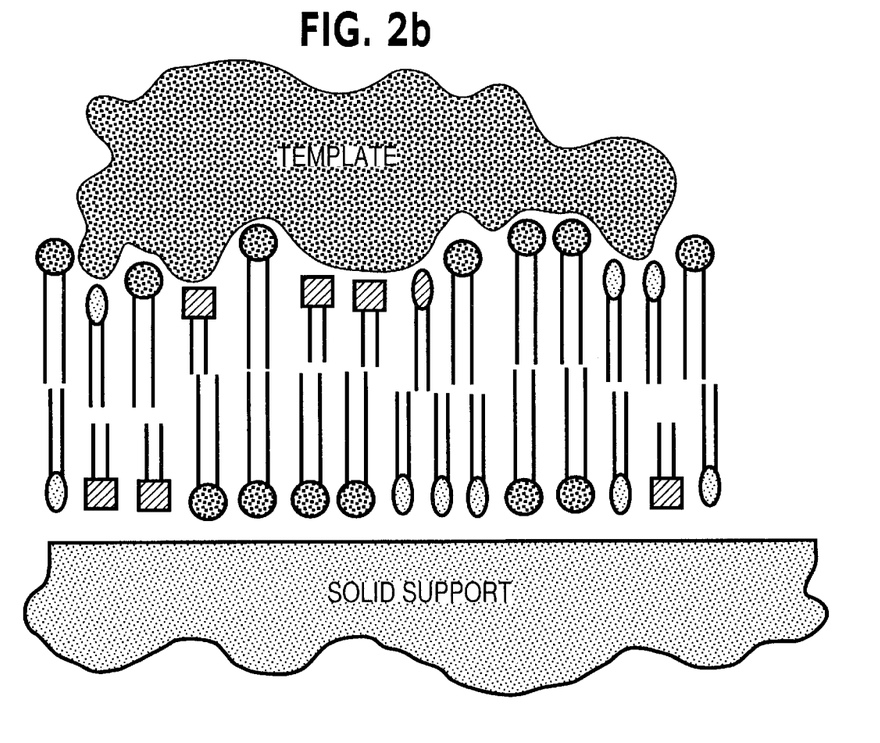
FIG. 2b shows a side-view schematic of the reversibly stabilized imprint of the template object of the bilayer from FIG. 2a after the transition of the bilayer to the gel- or crystalline phase state. Note that the template object is still present but is not anymore required to maintain the structure of the imprint.

As a result, a dynamic structuring of the bilayer will be established as is depicted in FIG. 2a. This structuring can be considered as a (local) partial demixing of the amphiphiles in the fluid bilayer state owing to the presence of the template surface. To obtain from this dynamic structuring a molecular imprint of the template in the bilayer now requires a transformation of the bilayer from its dynamic state into a more static one where all long range thermal motions that oppose the permanence of the structuring are reduced to a level rendering them to a minor disturbance or background. This is achieved by inducing the phase transition of the bilayer from the fluid- to the gel- or crystalline phase state. A convenient means (though not the only one) to achieve this is to lower the temperature of the bilayer below its phase transition temperature $T_m$. For the case of phospholipids, this causes their tails to assume an all-trans conformation and a simultaneous thickening of the bilayer by up to 10 Å while at the same time all long range diffusive motion is reduced to high frequency intramolecular vibrations of the lipids. This situation is depicted in FIG. 2b. The transition of the tails to an all-trans conformation increases the length differences between adjacent short-tailed and long-tailed lipids even more, and renders the molecular surface structuring sharper when compared to the fluid state of the bilayer.

The final step to obtain the molecular imprinted surface is now the removal of the predetermined biological molecule or particle that was used as a template. It is understood that this has to be done under conditions that keep the bilayer in the gel- or crystalline state. One skilled in the art knows how to remove molecules or particles adsorbed to surfaces. For example, a convenient way to achieve this for the case of a Coulomb interaction between template and surface is the application of a salt gradient at temperatures below the phase transition temperature. Another way of removing molecules, especially protein templates which are strongly bound to the imprint, is to digest the protein template by enzymatic reactions, for example, by a protease. The resulting amino acids or oligopeptides possess only small binding constants and are easily removed from the imprint. The digestion of proteins by proteases is a well known biochemical procedure.

Figure 3:
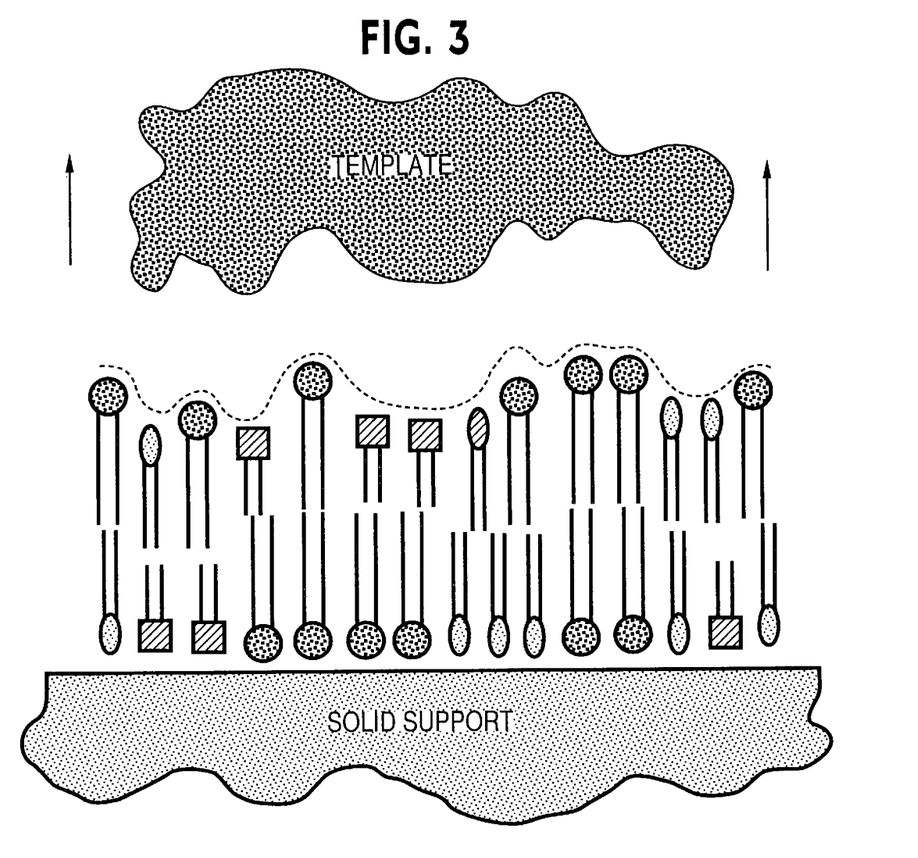
FIG. 3 shows a side-view schematic of a temporarily stabilized imprint derived from the template object from FIG. 2a after removal of the template in the gel- or crystalline phase state. Note that the imprint maintains its template specific structure even if minor structural relaxation e.g. bond rotations of functional groups in the amphiphile headgroups should occur.

Once the template molecule or particle is removed from the bilayer a molecular imprinted surface is created that retains the imprint as long as the bilayer remains-in the gel- or crystalline state (FIG. 3). Since, for the case of lipids, the whole preparation process takes place in an aqueous environment and the surface consists of molecules derived from natural lipids occurring in biological membranes, this surface is of highest biocompatibility. If proteins are used as a template, this may reduce or even prevent denaturation of both the template molecule during the imprinting process as well as of other molecules that undergo specific recognition and binding at the imprinted surface.

The invention also provides a method to delete the molecular imprint produced previously and to make the bilayer surface ready for molecular imprinting with another predetermined biological molecule or particle. The method includes the steps of: (a) transfer of the molecularly imprinted bilayer to the fluid phase state and (b) removal of any remains of the predetermined molecule or particle from the bilayer. Once produced, the stability of the molecular imprint depends on the maintenance of conditions that keep the bilayer in the gel- or crystalline phase state. If it becomes necessary to restructure the surface with molecular imprints of another predetermined biological molecule or particle or if the molecular imprinting is to be repeated with the same templates as used previously, the existing molecular imprint must be deleted first. This is achieved by transferring the bilayer to the fluid phase state which is most conveniently done by raising the temperature of the bilayer to values above its phase transition temperature. The onset of lateral diffusion upon crossing the phase transition temperature in ascending direction causes an almost instantaneous loss of surface structuring by the tendency of the thermally driven diffusion process to distribute all lipids homogeneously over the bilayer. A treatment to remove all remains of the template from the previously molecular imprinted surface leads to a state of the surface comparable to that prior to the first molecular imprinting (FIG. 1b). Those skilled in the art know how to treat a surface in order to detach a non-specifically interacting template from it without disturbing the surface integrity. For example, if the non-specific attractive interaction consists of a Coulomb interaction between the bilayer and the template, a flushing of the surface with an appropriate salt gradient will cause a complete removal of the template from the fluid phase bilayer without disturbing the bilayer integrity. After this procedure, the process of molecular imprinting can be started over again as described in detail above. The number of repeats of the process of molecular imprinting and deleting is theoretically unlimited since the process of crossing of the phase transition temperature of a bilayer is known to be reversible.

As used herein, the term "specific recognition and binding" refers to a molecular imprinted surface that is recognized by a predetermined biological molecule or particle on the basis of the (complementary) matching of the three-dimensional structure of the imprint with part of the outer contour of the predetermined biological molecule or particle and a resulting binding between them.

The invention also provides a method of using a molecular imprinted surface for the separation of a predetermined biological molecule or particle from a material that contains the predetermined biological molecule or particle. The method includes the steps of: (a) contacting the molecular imprinted surface exhibiting three-dimensional molecular imprints of the predetermined biological molecule or particle with the material and allowing the specific recognition and binding of the predetermined biological molecule or particle to the surface; (b) separation of the surface from the material; (c) recovery of the predetermined biological molecule or particle from the molecular imprinted surface.

The contact between the imprinted surface, which was kept in its gel- or crystalline state upon imprinting, has to take place under gel- or crystalline phase state conditions. For example, the imprinted surface may be arranged within a thermostated container that can be filled with a fluid mixture containing the predetermined biological molecule or particle. The temperature of the container and the fluid mixture must be below the phase transition temperature of the imprinted surface. The contact may be ceased by removal of the fluid mixture and flushing the container with a washing fluid that removes all unbound molecules or particles and leaves the imprinted surface covered with the selectively recognized and bound predetermined biological molecule or particle. The elution of the predetermined biological molecule or particle from the surface can be achieved by flushing the surface with another washing medium. One skilled in the art knows which physicochemical and biological conditions to adjust in the washing medium to obtain a mild but efficient elution. For example, a widely used method for protein elution is the flushing with buffered salt or pH gradients.

Thus, in one embodiment, solid supported bilayers are used and the solid support consists of a solid which exhibits very low surface roughness on a molecular scale, such as silicon, mica, silica or a suitable polymer. The solid support is entirely coated with a single bilayer of bilayer forming amphiphiles and can be immersed (or dispersed for the case of solid particles) in a fluid. The composition of the bilayer is selected in a way that ensures that amphiphiles of at least two different molecular lengths are present. As an example, for the case of the phospholipid lecithin the bilayer may consist of saturated lecithins with different numbers of carbons in their hydrocarbon chains. Moreover, the composition of the bilayer is selected in a way to exhibit a phase transition between the fluid and the gel- or crystalline phase state at a phase transition temperature within a suitable range above the freezing point of the fluid and below temperatures that may damage the integrity of the predetermined biological molecule or particle or of the bilayer itself.

The non-selective attractive force between said surface and the predetermined biological molecule or particle being dissolved in the medium is readily obtained by Coulomb interaction (a) using an admixture of anionic or cationic amphiphiles to the bilayer or (b) employing the surface charge of the solid support in case that it is not completely electrically screened by the bilayer. Furthermore, non-specific attractive forces can be obtained by possible van-der Waals forces between the predetermined biological molecule or particle and the bilayer or by hydrophobic forces between the bilayer interior and the predetermined biological molecule or particle. Such hydrophobic forces may arise, in the case of proteins, via hydrophobic loops (i.e. hydrophobic amino acid residues of the protein that can partly penetrate the bilayer upon adsorption).

The phase state of the bilayer is adjusted by temperature control of the solid support and the surrounding fluid. Temperature control is achieved by arranging the supported bilayer and the surrounding fluid within a container whose temperature is adjustable. Lateral diffusion of the amphiphiles along the bilayer plane in the fluid phase state allows the alignment of the amphiphiles of different length along that part of the contour of the predetermined biological molecule or particle facing the bilayer. Those parts of the predetermined biological molecule or particle which are pressing deep into the bilayer will become enriched with short amphiphiles while other parts, located more distant from the bilayer, will attract longer amphiphiles. Once this distribution is organized, it is locked in place by lowering the temperature of the container below the phase transition temperature, thus forming a rigid three-dimensional imprinted surface where lateral diffusion is prevented. Removal of the template at temperatures below the phase transition temperature gives a three-dimensional imprinted surface attached to a solid, giving it sufficient rigidity to retain the imprinted structure for selective recognition and binding of the template.

The imprint of the template at the surface can be removed or deleted again by increasing the temperature above the phase transition temperature where the onset of lateral diffusion causes a complete loss of the three-dimensional imprint within an instant.

In a second embodiment the supported bilayer is replaced by a supported monolayer of the same amphiphile composition as discussed above. It has been shown by the work of Linseisen et al. [14], that supported monolayers of amphiphiles can be prepared on silica beads under conditions that the silica surface is prior made sufficiently hydrophobic by a treatment octadecyl-di-methyl-mono-chlorosilane. It has further been shown in the same work that the physical properties of this supported monolayer resemble those of the supported bilayer with respect to its phase transition behavior and the lateral diffusivity of the amphiphiles. The only relevant difference to the supported bilayer is that the amphiphile monolayer faces an octadecyl-silane surface which is in the gel- or crystalline state even at those temperatures where the amphiphile monolayer is fluid. Hence, the amplitude of the three-dimensional structuring of the surface can be expected to be reduced by up to 50% for the case of the supported monolayer compared to the supported bilayer. This is because the immobile octadecyl-silane does not contribute to the structuring of the surface while in the case of the supported bilayer both bilayer leaflets can act together to increase the modulation of the surface contour facing the bulk as is shown in FIG. 1b. Nevertheless, the reduced three-dimensional structuring of the supported monolayer can be used in the same way as described above for the supported bilayer. Thus, after the supported bilayer is replaced by the supported monolayer of identical amphiphile composition, all procedures for the production or deletion of molecular imprints and their use for selective recognition are completely analogous to those described above for supported bilayers. In a third embodiment, lipid bilayers dispersed in a fluid but without solid support are used as surface for imprinting. The bilayer composition has to meet the same criteria regarding the length of the different lipids and phase transition temperature of the amphiphile mixture as discussed above. Contact between the bilayer and the predetermined biological molecule or particle is established and maintained by the same methods as detailed above with the exception of the employment of the solid support surface charges.

Similarly, the locking of the bilayer forming amphiphiles in place after their alignment in the fluid phase state of the bilayer with adsorbed predetermined biological molecule or particle is achieved by lowering the temperature of the bilayer below the phase transition temperature. Then the template is removed and the bilayer retains its imprinted three-dimensional structure at temperatures below the phase transition temperature. Deletion of the imprinted structure is again achieved by raising the temperature of the bilayer above the phase transition temperature.

EXAMPLE I

Preparation of Bilayers and of Solid Supported Bilayers

This example describes the preparation of bilayers without and with solid support for an example in which the ternary lipid mixture used is made of 1,2-dielaidoyl-sn-glycero-3-phosphocholine (a synthetic zwitterionic phospholipid, denoted DEPC), 1,2-dimyristoyl-sn-glycero-3-phosphocholine (a synthetic zwitterionic phospholipid denoted DMPC) and di-tetradecyl-dimethyl-ammonium-bromide (a synthetic cationic lipid analog, denoted DTDAB). The composition was 20 mol-% DTDAB, 30 mol-% DEPC and 50 mol-% DMPC. Thus 30% of the lipids had C-18 tails and 70% had C-14 tails. The lyophilized lipids were dissolved at the corresponding weight ratio in 10 ml of a buffer medium denoted as buffer A (20 mM Hepes buffer, pH 7.2 containing 20 mM NaCl) at a concentration of 15 mg lipids per ml of buffer A and a temperature of 30° C. The dispersion was incubated for 15 minutes at this temperature under gentle vortexing. After this, the dispersion was sonicated with a rod ultrasonicator at high power for 10–15 min. until the previously milky dispersion appeared to be optically clear. After the sonication, the solution consisted of small, unilamellar vesicles (SUV) with diameters in the range 40–100 nm (measured by electron microscopy) that could be used as bilayers. The phase transition temperature of the dispersion was determined by differential scanning calorimetry (DSC) to be about 24.0° C.

For the preparation of solid supported bilayers, the above SUV solution was brought into contact with a suitable solid support and incubated for 1 hour at 30° C. under gentle vortexing. Porous silica beads, so-called silica gels, were used as a solid support in order to achieve a high surface/volume ratio. The silica gels used had a pore diameter of about 400 nm and a bead diameter of about 10–15 $\mu$m according to the specification of the supplier. The pores were sufficiently big to allow the SUV to diffuse into them. Before mixing with the SUV solution, the silica gels were washed in a ten-fold volume of methanol and after this dried in vacuum for about 12 hours at a temperature of about 80° C. Upon contact with the silica surface, the SUV collapsed and formed a single bilayer that covers ultimately the whole gel surface. The amount of lipid and silica gel used in the preparation was calculated such that the lipid was in 50% excess to the amount required to coat the whole surface of the gel (including the inner surface of the pores) with a single bilayer, assuming 80 Å$^2$ as the surface area per lecithin molecule. Thus, about 5 g of silica gel were used for about 150 mg of lipid mixture. After the one hour incubation, the silica gel dispersion was washed 3 times in 100 ml of buffer A at about 30° C. in order to remove all excess SUV. The remaining silica gel dispersion represents a single bilayer on a solid support system. The phase transition temperature of this silica gel is about 24° C. as determined by differential scanning calorimetry.

EXAMPLE II
Preparation of Imprinted Surfaces Using Protein Templates.

This example demonstrates that a supported bilayer prepared as above can be imprinted with a protein as template.

A standard gel chromatography column of 10 mm diameter and 20 cm length, equipped with a standard thermostatable water jacket was packed with 5 grams of the bilayer coated silica gel prepared as described above. The packing procedure is analogous to that employed in standard gel chromatographic applications and is therefore known to those skilled in the art. Then the column was flushed with buffer A at flow rate of 2 ml/min for about 1 h at a temperature of about 4° C. by circulating water of this temperature through the jacket. The water temperature was controlled by a water bath thermostat. After this, the column temperature was raised to about 30° C. and the flushing continued at the same rate for another hour.

The template protein used in this example was trypsin inhibitor from bovine pancreas which exhibits an isoelectric point of 4.6 and thus is negatively charged at neutral pH value. The protein was dissolved in buffer A at a concentration of 2 mg/ml. Since the supported bilayer contains cationic amphiphiles (DTAB), an attractive electrostatic interaction with the trypsin inhibitor can be expected.

At a column temperature of 30° C. (fluid phase state of the bilayer), 2 ml of the template solution (4 mg of protein) was applied to the column at a flow rate of 2 ml/min and the flow was stopped immediately after all the template protein entered the column gel. This application procedure is analogous to that used in standard gel chromatography and thus known to one skilled in the art. After a 12 h incubation at a suitable temperature to allow the template to settle at the supported bilayer, the temperature of the column was rapidly decreased down to 4° C. at a rate of 5 deg/s. This caused a phase transition of the supported bilayer with the coupled template from the fluid to the gel- or crystalline phase state. After this, the column was flushed at 4° C. for 1 h at a flow rate of 2 ml/min in order to remove all excess protein not electrostatically bound to the bilayer. A UV monitor at the column exit detecting the absorbance of the buffer at 280 nm indicated that no further proteins left the column after 15 min of flushing.

To remove the template from the imprinted gel- or crystalline phase bilayer, a salt gradient (NaCl in buffer A) was applied to the column at 4° C. according to procedures known to one skilled in the art. Elution of the template was observed by a peak of the UV monitor absorbance at about 410 mM NaCl. Further increase of the salt concentration up to 500 mM did not result in further elution of template protein. The column with the molecular imprinted supported bilayer was stored at 4° C. for 12 h before further use.

EXAMPLE III
Comparison of Substrate Binding Affinity for Imprinted and Non-imprinted Supported Bilayers.

This example demonstrates that the binding affinity of molecular imprinted supported bilayers for the protein used previously as a template is significantly higher than that of a non-imprinted supported bilayer.

A control column identical to the one described in Example II was set up and all flushings and temperature changes were applied analogously to the above example with the exception that no template protein was applied to the column. Thus, at the end of the preparation the supported bilayer of this control column is also in the gel- or crystalline phase state, but the distribution of the lipids was not influenced by the presence of a template. The control column with the non-imprinted supported bilayer was stored at 4° C. for 12 h before further use.

To compare the binding strength of trypsin inhibitor to imprinted and non-imprinted supported bilayer, 0.5 ml (1 mg trypsin inhibitor) each of the protein solution from example II was applied to the imprinted and control column at 4° C. and a flow rate of 2 ml/min. The columns were flushed with buffer A for 1 h after the protein application in order to remove all unbound protein from the column. After this, identical salt gradients were applied to both columns and protein elution was observed by UV monitor absorbance at 420 mM NaCl for the imprinted and at 270 mM NaCl for the non-imprinted supported bilayer. Integration of the recorded UV absorption peaks showed that at the respective salt concentrations, similar amounts of protein were eluted from each column. No further elutions were observed for both columns for salt concentrations up to 1 M NaCl. Verification that indeed the applied proteins gave rise to the absorbance peaks at 420 and 270 mM NaCl was achieved by subjecting the protein fractions collected at the corresponding salt concentrations to an SDS-PAGE analysis, an analytical technique known to those skilled in the art. After coomassie blue staining, the SDS gels showed one band only which corresponded in both cases to trypsin inhibitor.

The procedure of protein loading and subsequent elution by the salt gradient was repeated five times with both columns, the elution concentrations were all within ±10 mM NaCl of the values given above.

EXAMPLE IV
Deletion of a Molecular Imprint from a Supported Bilayer

This example demonstrates how a molecular imprint in a supported bilayer can be deleted by raising the temperature above the phase transition temperature.

The temperature of the imprinted column that was used in example III was increased from 4° C. to 30° C. at a heating rate of 0.1 deg/s and at a flow rate of 2 ml/min. Right after this, the column was cooled down to 4° C. at a rate of 5 deg/s and a flow of 2 ml/min.

2 ml (4 mg trypsin inhibitor) of the protein solution from Example II was applied to the column at 4° C. and the column was flushed at 2 ml/min with buffer A for one hour. Then a salt gradient was applied to the column at this temperature and elution of the protein was observed by the UV monitor peak at a salt concentration of 280 mM NaCl. No further elution was observed for NaCl concentrations up to 1 M. This salt concentration corresponds to that measured in example III for a non-imprinted supported bilayer. The heating and cooling of the column through the phase transition temperature caused a loss of the higher binding affinity of the supported bilayer as determined in example II for the protein.

EXAMPLE V
Restoring a Previously Deleted Imprint in a Supported Bilayer

This example demonstrates that a column where the imprint of a template has been deleted by the procedure described in example IV, can be re-imprinted again.

The column used in example IV was heated up again to 30° C. at a heating rate of 0.1 deg/s and a buffer A flow rate of 2 ml/min. At this temperature, the column was flushed with buffer A at the same flow rate for 1 h. After this the imprint procedure as described in detail in example II was initiated with the application of 2 ml (4 mg trypsin inhibitor) protein solution and all following steps were exactly as in example II. In order to test the column for increased affinity for trypsin inhibitor due to the imprint, 0.5 ml (1 mg trypsin inhibitor) of said protein solution from example II was applied to the column at 4° C. and at a flow rate of 2 ml/min. The column was flushed with buffer A for 1 h after the protein application in order to remove all unbound protein from the column. After this, a NaCl gradient was applied and protein elution was observed by UV monitor absorbance at 430 mM NaCl. This salt concentration corresponded within the error of the measurement to that observed in example III for the imprinted column. No further elution was observed for salt concentrations up to 1 M NaCl.

EXAMPLE VI
Effect of Lipid Chain Length on the Imprint

This example shows that the presence of electrically charged lipids in the bilayer is alone not sufficient to create an imprint that exhibits increased binding affinity for the protein used as template.

For examples I–V, a lipid bilayer composition was used that consisted of 30% lipids with C-18 tails and 70% with C-14 tails. Thus, the bilayer must exhibit regions enriched with C-18 where the bilayer is about 3–5 Å thicker than in the C-14 enriched regions. The surface profile of this bilayer on a molecular scale can thus be considered as a flat region of C-14 lipids with occasional elevated plateaus or peaks which are made up of the 30% C-18 lipids. The use of a bilayer consisting of 70% C-18 and 30% C-14 lipids should then give the inverse profile, i.e. flat regions of C-18 lipids with occasional indents of C-14 lipids. In this example, a mixture of 70% DEPC, 20% DTAB and 10% DMPC was used to coat the silica gel analogously to Example I. This lipid mixture exhibits a phase transition temperature of 18° C. as determined by DSC. The bilayer coated silica gel was subjected to the molecular imprinting procedure with trysin inhibitor as template as described in Example II and the binding affinity of trypsin inhibitor to this imprinted column was determined analogously to the procedure given in Example III. The elution of the protein after application of the salt gradient was observed at 280 nM NaCl. This value agreed within the experimental error with that obtained for the (non-imprinted) control column in Example III. This indicated that indeed no imprint which caused trypsin inhibitor binding was obtained for this mixture although its amount of charged lipid was identical to that of the column from Example II, which clearly showed higher trypsin inhibitor binding affinity.

EXAMPLE VII
The Use of Macromolecules Other than Trypsin Inhibitor as Templates.

This example demonstrates that the principles of molecular imprinting in supported bilayers as shown in Examples II–V are not restricted to the use of trypsin inhibitor as template. Substituting trypsin inhibitor in Examples II–V by other biological macromolecules and doing the experiment exactly as described in Example III gave elution NaCl concentrations of these proteins for imprinted and control column as listed in Table I. Note that the lipid mixture was identical to that from Example I for all measurements and that the same column was used for all different macromolecules as templates. The columns (imprinted and control column) were flushed with buffer A at 1 M NaCl, 30° C. and a flow rate of 2 ml/min for 1 h between the runs with different macromolecules. After these flushings, 100 μl of the bilayer coated silica gel were carefully removed with a microsyringe from the top of the gel bed of both imprint and control column. These samples were subjected to SDS-PAGE with subsequent Coomassie Blue staining in order to check the column for macromolecule contaminants left from the previous run. For all macromolecules listed in Table I, no contamination of the gel was detected. The concentrations of the macromolecule solutions (all were dissolved in buffer A) used in these experiments were identical to those given in the Examples II–V except for the DNA where a about 0.2 mg/ml solution was used and a total of 0.4 mg DNA were applied to the column.

TABLE I

NaCl concentrations in mM for macromolecule elution from imprinted and control columns

| Macromolecule | imprinted | control |
|---|---|---|
| Catalase | 380 | 250 |
| DNA (calf thymus) | 490 | 320 |
| Myelin Basic Protein (bovine brain) | 550 | 360 |
| b-Lactoglobulin | 430 | 280 |

EXAMPLE VIII
Binding Affinity of Imprinted Columns for Proteins Other than the One Used as Template.

This example demonstrates that imprinting a supported bilayer with a protein increases the binding affinity of this protein to the surfaces but leaves that of another protein unchanged.

A column imprinted with trypsin inhibitor according to the procedures given in Examples I and II was first tested for the presence of a molecular imprint according to the procedures given in Example III. Elution of the trypsin inhibitor was detected at a NaCl concentration of 410 mM, thus indicating the presence of an imprint. After flushing the column with buffer A at 1 M NaCl, 4° C. column temperature and 2 ml/min flow rate, 0.5 ml of catalase solution (1 mg catalase in buffer A) were applied at the same temperature and flow rate. The procedure given in Example III was repeated and elution of catalase was detected at a NaCl concentration of 240 mM. A comparison with the value given in Table II shows that this corresponds to the catalase binding affinity measured for a non-imprinted column. In order to check whether the trypsin inhibitor imprint was retained after the passage of catalase through the imprinted column, the experiment was repeated with trypsin inhibitor after the column was flushed for 1 h at 1 M NaCl. The result for trypsin inhibitor was identical to that measured before the catalase application, i.e. elution was detected at 420 mM NaCl.

After this, the molecular imprint of this column was deleted by following the procedures given in Example IV. This deletion was confirmed by another loading of the column with trypsin inhibitor at 4° C. and detection of its elution at 280 mM NaCl.

PUBLICATIONS (1) Wulff, G. Molecular imprinting in crosslinked materials with the aid of molecular templates—a way towards artificial antibodies. Angew. Chem., Int. Ed. Engl. 1995, 34, 1812–1835.

(2) Steinke, J.; Sherrington, D. C.; Dunkin, I. R. "Imprinting of Synthetic Polymers Using Molecular Templates"; in: Advances in Polymer Science, Vol. 123, (Ledwith, P., Ed.), Springer Verlag: Berlin, Heidelberg, 1995; 81–125.

(3) Sagiv, J. Organized Monolayers by Adsorption.1. Formation and Structure of Oleophobic Mixed Monolayers on Solid Surfaces. J. Am. Chem. Soc. 1980, 102, 92–98.

(4) Wulff, G.; Heide, B.; Helfmeier, G. J. Am. Chem. Soc. 1986, 108, 1089–91.

(5) Yamamura, K.; Hatakeyama, H.; Naka, K.; Tabushi, I.; Kurihara, K. J. Chem. Soc., Chem. Commun. 1988, 79–81.

(6) Kamino, A.; Koyano, H.; Ariga, K.; Kunitake, T. Control of the Molecular Packing in Guadinium Monolayers through Binding with Aqueous Polycarboxylates. Bull. Chem. Soc. Jpn. 1996, 69, 3619–3631.

(7) Kunitake, T. Molecular Recognition by Molecular Monolayers, Bilayers, and Films. Thin Solid Films 1996, 284–285, 9–12.

(8) Oishi, Y.; Torii, Y.; Kuramori, M.; Suehiro, K.; Ariga, K.; Taguchi, K.; Kamino, A.; Kunitake, T. Two-dimensional Molecular Patterning through Molecular Recognition. Chem. Lett. 1996, 411–412.

(9) Oishi, Y.; Kato, T.; Kuramori, M.; Suehiro, K.; Ariga, K.; Kamino, A.; Koyano, H.; Kunitake, T. Atomic Force Microscopic Observation of Random Molecular Arrangement in Dialkyl Guanidinium Monolayer. Chem. Lett. 1996, 857–858.

(10) Oishi, Y.; Torii, Y.; Kato, T.; Kuramori, M.; Suehiro, K.; Ariga, K.; Taguchi, K.; Kamino, A.; Koyano, H.; Kunitake, T. Molecular Patterning of a Guadinium/Orotate Mixed Monolayer through Molecular Recognition with Flavin Adenine Dinucleotide. Langmuir 1997, 13, 519–524.

(11) Arnold, F. H.; Dhal, P.; Shnek, D.; Plunkett, S. "Composition of Matter Comprising an Imprinted Matrix Exhibiting Selectice Binding Interactions Through Chelated Metals"; U.S. Pat. No. 5,310,648, 1994.

(12) Shnek, D. R.; Pack, D. W.; Sasaki, D. Y.; Arnold, F. H. Specific Protein Attachment to Artificial Membranes via Coordination to Lipid-Bound Copper(II). Langmuir 1994, 10, 2382–2388.

(13) Ng, K.; Pack, D. W.; Sasaki, D. Y.; Arnold, F. H. Engineering Protein-Lipid Interactions —Targeting of Histidine-Tagged Proteins to Metal-Chelating Lipid Monolayers. Langmuir 1995, 11, 4048–4055.

(14) Linseisen, F.; Hetzer, M.; Brumm, T.; Bayerl, T. M. Differences in the physical properties of lipid monolayers and bilayers on a spherical solid support. Biophysical Journal 1997, 72, 1659–1667.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

What is claimed is:

1. A composition which changes its dynamic state through non-covalent interaction with a template object comprising:

imprinted amphiphilic molecules having hydrophobic tail groups and hydrophilic head groups which form a three-dimensional molecular imprinted surface at a solid/liquid interface; wherein said three-dimensional molecular imprinted surface of said imprinted amphiphilic molecules is formed by bringing a template object in close contact with a non-imprinted surface of amphiphilic molecules to form the three-dimensional molecular imprinted surface; and wherein said composition is reversibly switched between a fluid state and a solid state by variation of a physical parameter of said composition.

2. The composition of claim 1 wherein said three-dimensional molecular imprinted surface is formed by the steps of:

a) contacting said template object and said non-imprinted surface of amphiphilic molecules in a contact area which becomes said three-dimensional molecular imprinted surface, under conditions in which the non-imprinted surface of amphiphilic molecules is in a fluid state in which there is unrestricted diffusivity of said amphiphilic molecules of said non-imprinted surface within a linear plane of said non-imprinted surface of amphiphilic molecules and a spatially restricted diffusivity perpendicular to said linear plane;

b) allowing said non-imprinted surface of amphiphilic molecules to interact with a contour of said template object by a thermally driven local redistribution of surface amphiphilic molecules in the contact area between the non-imprinted surface of amphiphilic molecules and template object to minimize the free interaction energy between the contour of the template object and the non-imprinted surface of amphiphilic molecules, such that (i) protruding parts of the template object press deep into the non-imprinted surface of amphiphilic molecules, while other regions of the template object press less deep than the protruding parts of said template object into said amphiphilic molecules, and wherein said protruding parts are spatially complemented by short amphiphilic molecules and said other parts of said template object are spatially complemented by longer amphiphilic molecules; and wherein (ii) amphiphilic molecules of different chemical composition in their hydrophilic headgroups carry excess electrical charges and arrange to complement functional groups exhibited at the template object contour, and wherein amphiphilic molecules which carry electrical charles complement opposite charges at the template object contour, and form a three-dimensional molecular imprinted surface;

c) immobilizing the three-dimensional molecular imprinted surface formed in step (b), by a change of a physical parameter, from a fluid state to a solid state, in which the diffusive mobility of the amphiphilic molecules comprising the non-imprinted surface of amphiphilic molecules is inhibited in any direction over dimensions that exceed the spacing between two adjacent amphiphilic molecules, over a prolonged period of time; and d) removing said template object under conditions in which the three-dimensional molecular imprinted surface remains in said solid state to retain a three-dimensional molecular imprint.

3. The composition of claim 2 wherein said thee-dimensional molecular imprinted surface is transferred to its original, non-imprinted state by the steps of a) transferring the three-dimensional molecular imprinted surface from said solid state to said fluid state under conditions in which the three-dimensional molecular imprinted surface is not in contact with the template object, thereby re-establishing the diffusive mobility of all amphiphilic molecules comprising the three-dimensional molecular imprinted surface; and b) allowing the three-dimensional molecular imprinted surface to equilibrate at the fluid state for a time sufficient to allow constituent amphiphilic molecules to distribute randomly via diffusion.

4. The composition of claim 1 wherein said physical parameter is the temperature of said surface.

5. The composition of claim 1 wherein said amphiphilic molecules are lipids selected from the group consisting of dialkylphosphatidylcholines, dialkylphosphatidyl-ethanolamines, dialkylphosphatidylphosphatidic acids, dialkylphosphatidyl-phosphatidylserines, and dialkylphosphatidylphosphatidyl-glycerols.

6. The composition of claim 5 wherein alkyl groups of said dialkylphosphatidyl-cholines, dialkylphosphatidyl-ethanolamines, dialkylphosphatidyl-phosphatidic acids, dialkylphosphatidyl-phosphatidylserines, and dialkylphosphatidylphosphatidyl-glycerols, are derived from myristoyl, palmitoyl or stearoyl residues.

7. The composition of claim 1 wherein said amphiphilic molecules are lipids that have hydrophilic head groups containing molecules selected from the group consisting of carboxy groups, amino groups, tetraalkylammonium groups, sugar ring groups, alcoholic groups, polyoxyethyleneoxide groups and peptide residue groups.

8. The composition of claim 7 wherein said tetraalkylammonium groups are selected from an N,N-dialkyl group and an N,N-dimethylammonium group.

9. The composition of claim 1, wherein the three-dimensional molecular imprinted surface is a bilayer of said amphiphilic molecules.

10. The composition of claim 9, wherein the three-dimensional molecular imprinted surface is a bilayer of said amphiphilic molecules on a solid support.

11. The composition of claim 1, wherein the three-dimensional molecular imprinted surface is a monolayer of amphiphilic molecules on a hydrophobic solid support.

12. The composition of claim 1 wherein said template is a macromolecule selected from the group consisting of a protein, a peptide, an antigen, a DNA, a RNA, rigid polyampholytes, polyelectrolytes, co-polymers of polyions and co-polymers of polyzwitterions.

13. The composition of claim 1 wherein said template is a cell, a part of a cell, a virus or a part of a virus.

14. The composition of claim 2 wherein the contact between template and non-imprinted surface comprises molecular interactions between the amphiphilic molecules and the template which are selected from the group consisting of electrostatic, steric, hydrogen bond, and a combination of these interactions; and which minimizes the total interaction free energy between the surface non-imprinted and template.

15. The composition of claim 10 wherein the solid support is a porous or non-porous silica gel.

16. The composition of claim 11 wherein said hydrophobic solid support is obtained by coating a solid surface using a hydrophobic moiety which results in the formation of a hydrophobic surface coating via the formation of covalent bonds between the solid surface and a hydrophobic moiety.

17. The composition of claim 16 wherein said hydrophobic solid support is silica which is obtained by treatment with silane compounds.

18. The composition of claim 1 wherein the template object has minimum dimensions which allow for at least two independent interactions with two chemical functional groups of the amphiphilic molecules and the maximum dimension of the template object is smaller than an object which exposes said solid/liquid interface.

19. The composition of claim 10 wherein said solid support is in the form of a colloid, a gel or latex particles.

20. The composition of claim 1, wherein said composition is a diagnostic which detects a template macromolecule selected from the group consisting of a protein, a peptide, an antigen, a DNA, a RNA, rigid polyampholytes, polyelectrolytes, co-polymers of polyions and co-polymers of polyzwitterions.

* * * * *